(12) United States Patent
Nishiyama et al.

(10) Patent No.: US 7,807,426 B2
(45) Date of Patent: Oct. 5, 2010

(54) PROCESSES FOR PRODUCING OPTICALLY ACTIVE 1-SUBSTITUTED 2-METHYLPYRROLIDINE

(75) Inventors: Akira Nishiyama, Takasago (JP); Naoaki Taoka, Takasago (JP); Narumi Kishimoto, Takasago (JP); Nobuo Nagashima, Takasago (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/586,337

(22) PCT Filed: Jan. 19, 2005

(86) PCT No.: PCT/JP2005/000575

§ 371 (c)(1),
(2), (4) Date: Jul. 14, 2006

(87) PCT Pub. No.: WO2005/073388

PCT Pub. Date: Aug. 11, 2005

(65) Prior Publication Data

US 2007/0292926 A1    Dec. 20, 2007

(30) Foreign Application Priority Data

Jan. 30, 2004  (JP) .............................. 2004-023946

(51) Int. Cl.
C12P 7/18   (2006.01)
C12P 7/00   (2006.01)

(52) U.S. Cl. ........................................ 435/158; 435/132
(58) Field of Classification Search .................... None
See application file for complete search history.

(56) References Cited

U.S. PATENT DOCUMENTS 4,088,666 A    5/1978   Langer, Jr. et al.
4,156,603 A    5/1979   Langer, Jr. et al.
4,165,330 A    8/1979   Whitney et al.

FOREIGN PATENT DOCUMENTS

JP    49-55629 A    5/1974

OTHER PUBLICATIONS

Wada, et al. (1998) Biosci. Biotechnol. Biochem., 62(2): 280-85.*
Wada, et al. (1999) Journal of Bioscience and Bioengineering, 87(2): 144-48.*
Morrison and Boyd (1974) Organic Chemistry, 3rd Edition, Published by Allyn and Bacon, New York, NY., pp. 680 and 853 only.*
Morrison and Boyd (1974) Organic Chemistry, $3^{rd}$ Ed., by Allen and Bacon, New York, NY., pp. 680-681 and 853-854.*
Goto, et al. (1990) Proc Natl Acad Sci, USA, 87: 573-77.*
Yatagai, et al. (1990) J Chem Soc Perkin Trans, 4: 1826-1828.*
Yamada, et al. (2003) Chem Eur J, 9: 4485-09.*
Fujii, et al. (1996) Journal of the American Chemical Society, 118: 2521-22.*
Thomas A. Whitney, et al, "Asymmetric Synthesis via Lithium Chelates", Advances in Chemistry Series, vol. 130, 1974, pp. 270-280.
Thomas A. Whitney, et al, "Asymmetric Synthesis via Lithium Chelates", Polymer Preprints (American Chemical Society), vol. 13, No. 2, 1972, pp. 688-692.
A.B. Letunova, et al, Preparation of γ-Acetopropyl Alcohol From γ-Butyrolactone., Khimiko-Farmatsevticheskii Zhurnal, vol. 11, No. 12, 1977, pp. 121-123.
Mahn-Joo Kim, et al, "The Efficient Resolution of Protected Diols and Hydroxy Aldehydes by Lipases: Steric Auxiliary Approach and Synthetic Applications", Bioorganic & Medicinal Chemistry Letters, vol. 6, No. 1, 1996, pp. 71-76.
Bendicht Wermuth, "Purification and Properties of an Nadph-Dependent Carbonyl Reductase From Human Brain", Relationship to Prostaglandin 9-Ketoreductase and Xenobiotic Ketone Reductase, The Journal of Biological Chemistry, vol. 256, No. 3, 1981, pp. 1206-1213.
Joerg Peters, et al, "A Novel Nadh-Dependent Carbonyl Reductase with an Extremely Broad Substrate Range From Candida Parapsilosis: Purification and Characterization", Enzyme and Microbial Technology, vol. 15, Nov. 1993, pp. 950-958.

* cited by examiner

Primary Examiner—Robert M Kelly
(74) Attorney, Agent, or Firm—Sughrue Mion, PLLC

(57) ABSTRACT

The present invention relates to a process for producing an optically active 1,4-pentanediol by asymmetrically reducing 5-hydroxy-2-pentanone, which is easily available at low cost. The present invention also relates to a process for producing an optically active 1-substituted 2-methylpyrrolidine including sulfonylating the optically active 1,4-pentanediol to convert it to an optically active sulfonate compound, and reacting the compound with an amine. According to the processes of the present invention, an optically active 1,4-pentanediol and an optically active 1-substituted 2-methylpyrrolidine, which are useful as an intermediate for medicines and an intermediate for agricultural chemicals, can be simply produced from an inexpensive starting material.

3 Claims, No Drawings

PROCESSES FOR PRODUCING OPTICALLY ACTIVE 1-SUBSTITUTED 2-METHYLPYRROLIDINE

RELATED APPLICATION

This application is a national stage of PCT application PCT/JP2005/000575 filed on Jan. 19, 2005, claiming priority based on Japanese Application No. 2004-023946 (Jan. 30, 2004), the contents of which are incorporated herein by reference in their entirety.

TECHNICAL FIELD

The present invention relates to a process for producing an optically active 1-substituted 2-methylpyrrolidine, which is useful as an intermediate for medicines, agricultural chemicals, and the like. The present invention also relates to a process for producing an optically active 1,4-pentanediol, which is useful as a synthetic intermediate in the above process.

BACKGROUND ART

The following processes are known as a process for producing an optically active 1-substituted 2-methylpyrrolidine.
(1) A process for producing (R)-1-benzyloxycarbonyl-2-methylpyrrolidine including converting a hydroxyl group of L-prolinol derived from L-proline to a chloro group with thionyl chloride, protecting a nitrogen atom with a benzyloxycarbonyl group, and radically reducing the product with tributyltin hydride (Non-Patent Document 1).
(2) A process of optically resolving racemic 2-methylpyrrolidine with tartaric acid (Non-Patent Document 2).

However, process (1) includes many steps and uses a highly toxic tin compound. In process (2), crystallization must be repeated a plurality of times, and thus the operation is complex. Thus, any of these processes is not an industrially advantageous process.

If an optically active 1-substituted 2-methylpyrrolidine is derived using an optically active 1,4-pentanediol as a starting material, the above problem would be solved to efficiently produce an optically active 1-substituted 2-methylpyrrolidine. However, any known process for producing the optically active 1,4-pentanediol is not an industrially advantageous process.

For example, the following processes are reported as a process for producing an optically active 1,4-pentanediol.
(3) A process for producing (S)-1,4-pentanediol including coupling an enolate prepared from 2,4,4-trimethyl-2-oxazoline and n-butyllithium and (S)-epichlorohydrin, hydrolyzing the product with hydrochloric acid, and reducing the product with lithium aluminum hydride (Non-Patent Document 3).
(4) A process for producing (S)-1,4-pentanediol including treating D-glutamic acid with nitrous acid to produce γ-butyrolactone-4-carboxylic acid, reducing the carboxylic acid with borane-dimethyl sulfide complex to produce an alcohol, tosylating the hydroxyl group, and reducing the product with lithium aluminum hydride (Non-Patent Document 4).
(5) A process for producing (S)-1,4-pentanediol including reducing a carbonyl group of an ester of levulinic acid (ester of 4-oxopentanoic acid) with baker's yeast, and reducing the product with lithium aluminum hydride (Non-Patent Document 5).
(6) A process for producing (R)-1,4-pentanediol including protecting a hydroxyl group at the 1-position of racemic 1,4-pentanediol with a trityl group, asymmetrically acylating the product with a lipase, separating an ester from the resulting mixture of the ester and an alcohol, and deprotecting with p-toluenesulfonic acid (Non-Patent Document 6).

However, processes (3) and (4) include many steps and require using many expensive reagents. In process (5), the yield of the reductive reaction by the microorganism is low, 60% at the maximum. Furthermore, process (6) is a racemic resolution and thus inefficient.

[Non-Patent Document 1] J. Org. Chem., 1989, Vol. 54, pp. 209-216

[Non-Patent Document 2] Acta. Pharm. Suec., 1978, Vol. 15, pp. 255-263

[Non-Patent Document 3] J. Chem. Soc., Chem. Commun., 1994, pp. 483-484

[Non-Patent Document 4] J. Med. Chem., 1982, Vol. 25, pp. 943-946

[Non-Patent Document 5] Synthetic Communications, 1990, Vol. 20, pp. 999-1010

[Non-Patent Document 6] Bioorganic & Medicinal Chemistry Letters, 1996, Vol. 6, pp. 71-76

DISCLOSURE OF INVENTION

Problems to Be Solved by the Invention

In view of the above situation, it is an object of the present invention to provide an efficient process for producing an optically active 1,4-pentanediol. Furthermore, it is an object of the present invention to provide a process for simply and efficiently producing an optically active 1-substituted 2-methylpyrrolidine from the optically active 1,4-pentanediol.

Means for Solving the Problems

As a result of intensive studies, the present inventors have developed a process for simply producing an optically active 1,4-pentanediol by asymmetrically reducing 5-hydroxy-2-pentanone, which is easily available at low cost. The present inventors have also developed a process for simply producing an optically active 1-substituted 2-methylpyrrolidine by sulfonylating the optically active 1,4-pentanediol to convert it to an optically active sulfonate compound, and reacting the compound with an amine.

Namely, the present invention provides a process for producing an optically active 1,4-pentanediol represented by formula (2):

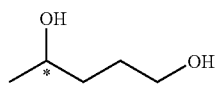

(2)

(wherein * represents an asymmetric carbon atom) by asymmetrically reducing 5-hydroxy-2-pentanone represented by formula (1):

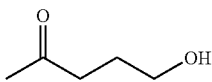
(1)

The present invention also provides a process for producing an optically active 1-substituted 2-methylpyrrolidine represented by formula (4):

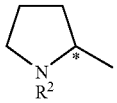
(4)

(wherein $R^2$ represents a hydrogen atom, a hydroxyl group, a methoxy group, a benzyloxy group, a substituted or unsubstituted alkyl group having 1 to 12 carbon atoms, a substituted or unsubstituted aralkyl group having 7 to 12 carbon atoms, or a substituted or unsubstituted aryl group having 6 to 12 carbon atoms, and * represents an asymmetric carbon atom) including sulfonylating the optically active 1,4-pentanediol represented by said formula (2) to convert it to an optically active disulfonate compound represented by formula (3):

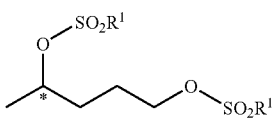
(3)

(wherein $R^1$ represents a substituted or unsubstituted alkyl group having 1 to 12 carbon atoms, a substituted or unsubstituted aralkyl group having 7 to 12 carbon atoms, or a substituted or unsubstituted aryl group having 6 to 12 carbon atoms, and * represents an asymmetric carbon atom), and reacting the compound with an amine.

ADVANTAGES OF THE INVENTION

According to the present invention, an optically active 1,4-pentanediol and an optically active 1-substituted 2-methylpyrrolidine, which are useful as intermediates for medicines or agricultural chemicals, can be simply produced at low cost from an inexpensive and easily available starting material.

BEST MODE FOR CARRYING OUT THE INVENTION

First, a starting material used in the present invention and products will be described. 5-Hydroxy-2-pentanone, which is the starting material of the present invention, is represented by formula (1):

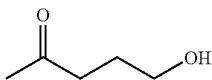
(1)

This compound is available at low cost. Alternatively, 5-hydroxy-2-pentanone can be simply produced by hydrolyzing 2-acetyl-γ-butyrolactone represented by formula (5):

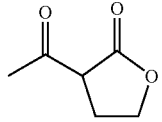
(5)

which is less expensive and easily available, in the presence of an acid such as phosphoric acid, sulfuric acid, nitric acid, or methanesulfonic acid.

When 5-hydroxy-2-pentanone represented by said formula (1) is stored at a high concentration, the purity thereof may be decreased because of dehydration condensation by itself. Alternatively, 5-hydroxy-2-pentanone may be stored in the form of an acidic aqueous solution of the compound (1) prepared by hydrolyzing 2-acetyl-γ-butyrolactone represented by said formula (5) in the presence of an acid, or an aqueous solution prepared by neutralizing the aqueous acid according to need. In such a case, the above problem does not occur, and the aqueous solution can be used as a starting material of the asymmetric reductive reaction without further treatment.

An optically active 1,4-pentanediol, which is a product of the present invention, is represented by formula (2):

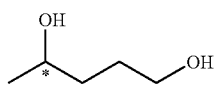
(2)

In the formula, * represents an asymmetric carbon atom and the absolute configuration thereof is R or S. Herein, R represents all the cases where, among both enantiomers, the R isomer is excessively included. Similarly, S represents all the cases where, among both enantiomers, the S isomer is excessively included.

An optically active disulfonate compound, which is a product of the present invention, is represented by formula (3):

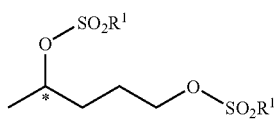
(3)

In the formula, $R^1$ represents a substituted or unsubstituted alkyl group having 1 to 12 carbon atoms, a substituted or unsubstituted aralkyl group having 7 to 12 carbon atoms, or a substituted or unsubstituted aryl group having 6 to 12 carbon atoms.

Preferably, $R^1$ is methyl group, ethyl group, chloromethyl group, trifluoromethyl group, benzyl group, phenyl group, 4-methylphenyl group, 4-chlorophenyl group, 2-nitrophenyl group, 3-nitrophenyl group, 4-nitrophenyl group, or the like. More preferably, $R^1$ is methyl group or 4-methylphenyl group. Symbol * represents the same as the above.

An optically active 1-substituted 2-methylpyrrolidine, which is a product of the present invention, is represented by formula (4):

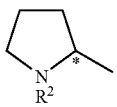
(4)

In the formula, $R^2$ represents a hydrogen atom, hydroxyl group, methoxy group, benzyloxy group, a substituted or unsubstituted alkyl group having 1 to 12 carbon atoms, a substituted or unsubstituted aralkyl group having 7 to 12 carbon atoms, or a substituted or unsubstituted aryl group having 6 to 12 carbon atoms.

Preferably, $R^2$ is hydrogen atom, hydroxyl group, methoxy group, benzyloxy group, methyl group, ethyl group, n-propyl group, tert-butyl group, allyl group, benzyl group, 1-phenethyl group, phenyl group, or methoxyphenyl group. More preferably, $R^2$ is benzyl group. Symbol * represents the same as the above.

Next, description will be made of a step of producing an optically active 1,4-pentanediol represented by said formula (2) by asymmetrically reducing 5-hydroxy-2-pentanone represented by formula (1). Examples of the process of asymmetric reduction in this step include, but are not limited to, a process of reduction with a hydride reducing agent modified with an optically active compound, a process of hydrogenation in the presence of an asymmetric transition metal catalyst, a process of performing a hydrogen transfer reduction in the presence of an asymmetric transition metal catalyst, and a process of reduction with a microorganism or an enzyme derived from a microorganism.

Specific examples of the hydride reducing agent modified with an optically active compound include a reducing agent prepared from an optically active tartaric acid and sodium borohydride, a reducing agent prepared from an optically active oxaborolidine derivative and borane, a reducing agent prepared from an optically active ketoiminato cobalt complex, sodium borohydride, and tetrahydrofuran-2-methanol, and a reducing agent prepared from optically active 1,1'-bi-2-naphthol and lithium aluminum hydride.

Preferred examples of the asymmetric transition metal catalyst used in the hydrogenation or the hydrogen transfer reduction include metal complexes of a Group VIII element in the periodic table, such as ruthenium, rhodium, iridium, or platinum. From the standpoint of the stability of the complex, availability, and economical efficiency, a ruthenium complex is more preferred.

A chiral ligand in the metal complex is preferably a phosphine ligand. As the phosphine ligand, a bidentate ligand is preferred. Examples of the bidentate ligand include BINAP derivatives such as BINAP (2,2'-bisdiphenylphosphino-1,1'-binaphthyl) and Tol-BINAP (2,2'-bis(di-p-tolylphosphino-1, 1'-binaphthyl); BDPP (2,4-bis(diphenylphosphino)pentane); DIOP (4,5-bis(diphenylphosphinomethyl)-2,2-dimethyl-1, 3-dioxane; BPPFA (1-[1',2-bis(diphenylphosphino)ferrocenyl]ethylamine); CHIRAPHOS (2,3-bis(diphenylphosphino)butane); DEGPHOS (1-substituted 3,4-bis(diphenylphosphino)pyrrolidine); DuPHOS (1,2-bis(2,5-substituted phospholano)benzene); and DIPAMP (1,2-bis[(o-methoxyphenyl)phenylphosphino]ethane).

The asymmetric reduction can be performed with hydrogen gas or a compound that can provide hydrogen, such as isopropanol, formic acid, or ammonium formate, in the presence of the asymmetric transition metal catalyst.

Alternatively, an optically active 1,4-pentanediol represented by said formula (2) can be produced by stereoselectively reducing the carbonyl group of 5-hydroxy-2-pentanone represented by said formula (1) in the presence of an enzyme source having the activity of stereoselectively reducing the carbonyl group.

The term "enzyme source" includes not only an enzyme itself having the above reduction activity but also a cultured product of a microorganism having the reduction activity. The term "cultured product of a microorganism" means a culture solution containing microbial cells, cultured microbial cells, or a processed product of the microbial cells. The term "processed product of the microbial cells" means, for example, a crude extract, lyophilized microbial cells, acetone-dried microbial cells, and a disrupted product thereof. Furthermore, these enzyme sources can be used in the form of an immobilized enzyme or an immobilized cell prepared by a known method. The immobilization can be performed by a method (for example, a cross-linking method, a physical adsorption method, or an entrapment method) known to those skilled in the art.

Examples of the enzyme source having the activity of stereoselectively reducing the carbonyl group of the compound represented by said formula (1) in the enzymatic reduction step of the present invention include enzyme sources derived from microorganisms selected from the group consisting of genus *Candida*, genus *Devosia*, genus *Rhodococcus*, and genus *Rhodotorula*.

Among the above enzyme sources, examples of the enzyme source having the activity of selectively reducing the carbonyl group of the compound represented by said formula (1) to produce the S-isomer include enzyme sources derived from microorganisms such as *Rhodococcus* sp. or *Rhodotorula glutinis*.

Examples of the enzyme source having the activity of selectively reducing the carbonyl group of the compound represented by said formula (1) to produce the R-isomer include enzyme sources derived from microorganisms such as *Candida magnoliae*, *Candida malis*, or *Devosia riboflavina*.

The microorganism having the ability of producing the reducing enzyme derived from a microorganism may be a wild strain or a mutant strain. Microorganisms derived by a genetic method such as a cell fusion or a genetic manipulation may also be used. Genetically manipulated microorganisms producing the enzyme can be obtained by, for example, a method including the steps of isolating and/or purifying the enzyme to determine a part or the whole of the amino acid sequence of the enzyme, obtaining the DNA sequence encoding the enzyme on the basis of the amino acid sequence, introducing the DNA into another microorganism to produce a recombinant microorganism, and culturing the recombinant microorganism to obtain the enzyme (WO98/35025).

The culture medium for a microorganism used as the enzyme source is not particularly limited as long as the microorganism can grow. An example of the culture medium that can be used is a normal liquid medium containing, as a carbon source, sugars such as glucose and sucrose, alcohols such as ethanol and glycerol, fatty acids such as oleic acid and stearic acid, esters thereof, and oil such as rape oil and soybean oil; as a nitrogen source, ammonium sulfate, sodium nitrate, peptone, casamino acid, corn steep liquor, wheat bran, and yeast extract; as inorganic salts, magnesium sulfate, sodium chloride, calcium carbonate, dipotassium hydrogenphosphate, and potassium dihydrogenphosphate; and as another nutrient source, malt extract and meat extract. The culture is aerobically performed. In general, the culture time is about 1 to 5 days, the pH of the culture medium is in the range of 3 to 9, and the culture temperature is in the range of 10° C. to 50° C.

The reductive reaction of the present invention can be performed by adding 5-hydroxy-2-pentanone serving as a substrate, a coenzyme NAD(P)H, and a cultured product of the microorganism or a processed product thereof into a suitable solvent, and stirring the mixture at an adjusted pH. An aqueous medium such as water or a buffer solution is usually used as a reaction solvent, but the reaction may be performed in a two-phase system including an organic solvent such as ethyl acetate or toluene and the aqueous medium.

The reaction conditions depend on the enzyme source used, the concentration of the substrate, and the like. The concentration of the substrate is generally about 0.1 to 100% by weight and preferably 1 to 60% by weight. The molar amount of the coenzyme NAD(P)H is generally 0.000001 to 1 times and preferably 0.000001 to 0.001 times the amount of the substrate. The reaction temperature is generally in the range of 10° C. to 60° C. and preferably in the range of 20° C. to 50° C. The pH during reaction is generally in the range of 4 to 9 and preferably in the range of 5 to 8. The reaction time is generally in the range of 1 to 120 hours and preferably in the range of 1 to 72 hours. The substrate may be added at one time or continuously. The reaction may be performed by a batch process or a continuous process.

In the reduction step of the present invention, by combining a commonly used coenzyme NAD(P)H regenerating system, the amount of consumption of the expensive coenzyme can be significantly reduced. A typical example of the NAD(P)H regenerating system is a method of using a glucose dehydrogenase and glucose.

When the reductive reaction is performed using a cultured product of a transformed microorganism prepared by introducing a gene of the reducing enzyme and a gene of an enzyme (for example, glucose dehydrogenase) having the ability of regenerating a coenzyme on which the reducing enzyme depends into a single host microorganism, an enzyme source required for regenerating the coenzyme need not be separately prepared. Thus, an optically active 1,4-pentanediol can be produced at lower cost.

An example of such a transformed microorganism is a transformed microorganism transformed with a plasmid having a DNA encoding the reducing enzyme and a DNA encoding the enzyme having the ability of regenerating the coenzyme on which the reducing enzyme depends. As the enzyme having the ability of regenerating the coenzyme, a glucose dehydrogenase is preferred and a glucose dehydrogenase derived from *Bacillus megaterium* is more preferred. As the host microorganism, *Escherichia coli* is preferred.

More preferably, examples thereof include *Escherichia coli* HB101 (pNTS1G) (Accession number: FERM BP-5835, Date of depositing: Feb. 24, 1997) transformed by a reducing enzyme gene derived from *Candida magnoliae* IFO0705 and a glucose dehydrogenase gene derived from *Bacillus megaterium*; *Escherichia coli* HB101 (pNTFPG) (Accession number: FERM BP-7117, Date of depositing: Apr. 11, 2000) transformed by a reducing enzyme gene derived from *Candida malis* IFO10003 and a glucose dehydrogenase gene derived from *Bacillus megaterium*; *Escherichia coli* HB101 (pNTDRG1) (Accession number: FERM BP-08458, a strain domestically deposited on May 29, 2002 was transferred to an international depositary under the Budapest Treaty) transformed by a reducing enzyme gene derived from *Devosia riboflavina* IFO13584 and a glucose dehydrogenase gene derived from *Bacillus megaterium*; *Escherichia coli* HB101 (pNTRS) (Accession number: FERM BP-08545, a strain domestically deposited on Feb. 13, 2002 was transferred to an international depositary under the Budapest Treaty) transformed by a reducing enzyme gene derived from *Rhodococcus* sp. KNK01; and *Escherichia coli* HB101 (pNTRGG1) (Accession number: FERM BP-7858, Date of depositing: Jan. 22, 2002) transformed by a reducing enzyme gene derived from *Rhodotorula glutinis* IFO415 and a glucose dehydrogenase gene derived from *Bacillus megaterium*. These transformed microorganisms have been deposited with International Patent Organism Depositary in National Institute of Advanced Industrial Science and Technology (Central 6, 1-1-1, Higashi, Tsukuba-shi, Ibaraki-ken, Japan).

When the reduction step of the present invention is performed in combination with a coenzyme regenerating system, or when a cultured product of the transformed microorganism or a processed product thereof is used as the enzyme source, a less expensive oxidized NAD(P) can be added as the coenzyme to perform the reaction.

The optically active 1,4-pentanediol produced by the reductive reaction can be purified by a known method. For example, when a microorganism or the like is used, a suspended substance such as the microbial cells is removed by a centrifugation, filtration, or the like according to need, the residue is subjected to extraction with an organic solvent such as ethyl acetate or toluene, and the organic solvent is removed under a reduced pressure to obtain a target compound. The target compound thus obtained has a purity that is sufficient for using in the subsequent step. However, in order to further increase the yield in the subsequent step or the purity of a compound prepared in the subsequent step, the purity of the target compound may be further increased by a general purification method such as fractional distillation or column chromatography.

Next, description will be made of a step of sulfonylating the optically active 1,4-pentanediol represented by said formula (2) to convert it to an optically active disulfonate compound represented by said formula (3). This step can be performed using a sulfonylating agent in the presence of a base.

Examples of the sulfonylating agent include sulfonyl halide and sulfonic acid anhydride. Examples of sulfonyl halide include methanesulfonyl chloride, ethanesulfonyl chloride, chloromethanesulfonyl chloride, benzylsulfonyl chloride, benzenesulfonyl chloride, 4-methylbenzenesulfonyl chloride, 4-chlorobenzenesulfonyl chloride, 2-nitrobenzenesulfonyl chloride, 3-nitrobenzenesulfonyl chloride, and 4-nitrobenzenesulfonyl chloride. Examples of sulfonic acid anhydride include trifluoromethanesulfonic anhydride. Among these, methanesulfonyl chloride or 4-methylbenzenesulfonyl chloride are preferred. The molar amount of the sulfonylating agent used is preferably 2 to 10 times and more preferably 2 to 4 times the amount of the compound (2).

The base is not particularly limited but tertiary amines are preferred. Examples thereof include triethylamine, tri-n-butylamine, N-methylmorpholine, N-methylpiperidine, diisopropylethylamine, pyridine, and N,N-dimethylaminopyridine. Triethylamine or pyridine is more preferred. The molar amount of the base used is preferably 2 to 100 times and more preferably 2 to 4 times the amount of the compound (2).

The base may also be used as a reaction solvent. Alternatively, the following solvents may be used as the reaction solvent. Examples thereof include ether solvents such as tetrahydrofuran, 1,4-dioxane, and ethylene glycol dimethyl ether; ester solvents such as ethyl acetate and isopropyl acetate; hydrocarbon solvents such as benzene, toluene, and hexane; ketone solvents such as acetone and methyl ethyl ketone; nitrile solvents such as acetonitrile and propionitrile; halogenated hydrocarbon solvents such as methylene chloride and chloroform; amide solvents such as N,N-dimethylformamide and N,N-dimethylacetamide; sulfoxide solvents such as dimethyl sulfoxide; urea solvents such as dimethylpropyleneurea; and phosphoric triamide solvents such as hexamethylphosphoric triamide. Among these, tetrahydrofuran, ethyl acetate, or toluene is preferred. These may be used alone or in combinations of two or more. When two or more types of the solvents are used, the mixing ratio is not particularly limited. The weight of the reaction solvent used is preferably 50 times or less and more preferably in the range of 5 to 20 times the weight of the compound (2).

From the standpoints of reducing the reaction time and improving the yield, the reaction temperature is preferably in the range of −20° C. to 150° C. and more preferably in the range of 0° C. to 100° C. The method of adding the optically active 1,4-pentanediol represented by said formula (2), the sulfonylating agent, the base, and the solvent, and the order of adding these components are not particularly limited.

As a treatment after the reaction, a general treatment for obtaining the product from the reaction solution is performed. For example, after the completion of the reaction, the reaction solution is neutralized by adding water, and according to need, an alkaline aqueous solution such as an aqueous solution of sodium hydroxide or an aqueous solution of sodium hydrogencarbonate, or an acidic aqueous solution such as an aqueous solution of hydrochloric acid or an aqueous solution of sulfuric acid, and an extraction operation is performed with a general extracting solvent such as ethyl acetate, diethyl ether, methylene chloride, toluene, or hexane. The reaction solvent and the extracting solvent are distilled off from the extract by, for example, heating under a reduced pressure, thus obtaining the target compound. The target compound thus obtained has a purity that is sufficient for using in the subsequent step. However, in order to further increase the yield in the subsequent step or the purity of a compound prepared in the subsequent step, the purity of the target compound may be further increased by a general purification method such as crystallization, fractional distillation, or column chromatography.

Next, description will be made of a step of producing an optically active 1-substituted 2-methylpyrrolidine represented by said formula (4) by reacting the optically active disulfonate compound represented by said formula (3) with an amine. This step can be performed by reacting with an excessive amine or reacting with an amine in the presence of a base.

Examples of the amine include ammonia, hydroxylamine, methoxyamine, benzyloxyamine, methylamine, ethylamine, n-propylamine, tert-butylamine, allylamine, benzylamine, 1-phenethylamine, aniline, and 4-methoxyaniline. Among these, benzylamine is preferred.

Examples of the base include alkali metal hydrides such as sodium hydride and potassium hydride; alkali metal alkoxides such as sodium methoxide, sodium ethoxide, and potassium tert-butoxide; alkali metal hydroxides such as lithium hydroxide, sodium hydroxide, and potassium hydroxide; alkali metal carbonates such as sodium carbonate and potassium carbonate; and tertiary amines such as triethylamine, tri-n-butylamine, N-methylmorpholine, N-methylpiperidine, diisopropylethylamine, pyridine, and N,N-dimethylaminopyridine. Among these, sodium hydroxide, potassium hydroxide, sodium carbonate, potassium carbonate, triethylamine, or pyridine is preferred.

The molar amount of the amine used is preferably 1 to 100 times and more preferably 1 to 10 times the amount of the compound (3). The molar amount of the base used is preferably 1 to 10 times and more preferably 1 to 5 times the amount of the compound (3).

The amine may also be used as a reaction solvent. Alternatively, the following solvents may be used as the reaction solvent. Examples thereof include water; alcohol solvents such as methanol, ethanol, and isopropanol; ether solvents such as tetrahydrofuran, 1,4-dioxane, and ethylene glycol dimethyl ether; ester solvents such as ethyl acetate and isopropyl acetate; hydrocarbon solvents such as benzene, toluene, and hexane; ketone solvents such as acetone and methyl ethyl ketone; nitrile solvents such as acetonitrile and propionitrile; halogenated hydrocarbon solvents such as methylene chloride and chloroform; amide solvents such as N,N-dimethylformamide and N,N-dimethylacetamide; sulfoxide solvents such as dimethyl sulfoxide; urea solvents such as dimethylpropyleneurea; and phosphoric triamide solvents such as hexamethylphosphoric triamide. Among these, tetrahydrofuran, ethyl acetate, or toluene is preferred. These may be used alone or in combinations of two or more. When two or more types of the solvents are used, the mixing ratio is not particularly limited. The weight of the reaction solvent used is preferably 50 times or less and more preferably in the range of 5 to 20 times the weight of the compound (3).

From the standpoints of reducing the reaction time and improving the yield, the reaction temperature is preferably in the range of −20° C. to 150° C. and more preferably in the range of 0° C. to 100° C. The method of adding the optically active disulfonate compound represented by said formula (3), the amine, the base, and the solvent, and the order of adding these components are not particularly limited.

As a treatment after the reaction, a general treatment for obtaining the product from the reaction solution is performed. For example, after the completion of the reaction, the reaction solution is neutralized by adding water, and according to need, an alkaline aqueous solution such as an aqueous solution of sodium hydroxide or an aqueous solution of sodium hydrogencarbonate, or an acidic aqueous solution such as an aqueous solution of hydrochloric acid or an aqueous solution of sulfuric acid, and an extraction operation is performed with a general extracting solvent such as ethyl acetate, diethyl ether, methylene chloride, toluene, or hexane. The reaction solvent and the extracting solvent are distilled off from the extract by, for example, heating under a reduced pressure, thus obtaining the target compound. The target compound thus obtained has a sufficient purity as an intermediate for synthesizing medicines, agricultural chemicals, or the like. However, the purity of the target compound may be further increased by a general purification method such as crystallization, fractional distillation, or column chromatography.

EXAMPLES

The present invention will now be described more specifically by way of examples. The present invention is not limited to the examples.

Example 1

Production of Optically Active 1,4-pentanediol

Each recombinant *Escherichia coli* shown in Table 1 was inoculated in 50 mL of 2×YT medium (tripeptone 1.6%, yeast extract 1.0%, NaCl 0.5%, pH=7.0) that was sterilized in a 500-mL Sakaguchi flask, followed by shaking culture at 37° C. for 18 hours. Subsequently, 10 mg of 5-hydroxy-2-pentanone, 1 mg of NAD or NADP, and 20 mg of glucose were added to 1 mL of the resulting culture solution, and the mixture was stirred at 30° C. for 20 hours. After the reaction, the reaction solution was subjected to extraction with 2 mL of ethyl acetate. Trifluoroacetic anhydride was added to the extract to perform derivatization. The O-TFA derivative product was then analyzed according to the following analytical method. The results are shown in Table 1.

[Analysis Condition]
Column: CHIRALDEX G-TA 20 m×0.25 mm I.D. (manufactured by ASTEC), Column temperature: 80° C., Split ratio: 100/1, Carrier gas: He 40 cm$^3$/sec, Detection: FID, Sample: O-TFA derivative Conversion rate (%)=amount of product/(amount of substrate+amount of product)×100

Optical purity (% ee)=(A−B)/(A+B)×100

(Each of A and B represents the amount of corresponding enantiomer, and A>B.)

TABLE 1

| Recombinant Escherichia coli | Coenzyme | Conversion rate (%) | Optical purity (% ee) | Absolute configuration |
|---|---|---|---|---|
| Escherichia coli HB101(pNTS1G) FERM BP-5835 | NADP | 100 | 99 | (R) |
| Escherichia coli HB101(pNTFPG) FERM BP-7117 | NAD | 100 | 99 | (R) |
| Escherichia coli HB101(pNTDRG1) FERM BP-08458 | NAD | 100 | 99 | (R) |
| Escherichia coli HB101(pNTRS) FERM BP-08545 | NAD | 100 | 99 | (S) |
| Escherichia coli HB101(pNTRGG1) FERM BP-7858 | NADP | 100 | 99 | (S) |

Example 2

Production of 5-hydroxy-2-pentanone

First, 100 mL of a 5% aqueous solution of phosphoric acid was added to 12.8 g (100 mmol) of 2-acetyl-γ-butyrolactone, and the mixture was stirred at 100° C. for 4 hours. The solution was cooled to room temperature, and the solution was then neutralized with an aqueous solution of sodium hydroxide to obtain an aqueous solution of 5-hydroxy-2-pentanone (130 g, 7.8% by weight).

Example 3

Production of (S)-1,4-pentanediol

Recombinant Escherichia coli HB101 (pNTRGG1) with an accession number of FERM BP-7858 was inoculated in 50 mL of 2×YT medium (tripeptone 1.6%, yeast extract 1.0%, NaCl 0.5%, pH=7.0) that was sterilized in a 500-mL Sakaguchi flask, followed by shaking culture at 37° C. for 20 hours. An aqueous solution (32 g) containing 2.5 g of 5-hydroxy-2-pentanone produced in Example 2, 2.5 mg of NADP, 6.6 g of glucose were added to 50 mL of the resulting culture solution. The solution was stirred at 30° C. for 24 hours while the pH of the solution was adjusted to 6.5 by adding a 7.5 M aqueous solution of sodium hydroxide dropwise. After the reaction, 50 mL of ethyl acetate was added to perform an extraction. The organic layer was distilled off under a reduced pressure. Thus, 2.6 g of (S)-1,4-pentanediol was obtained as a light brown oily substance (yield: 100%).

The optical purity of the product was measured by the same method as that in Example 1. The product had an optical purity of 99% ee or more.

$^1$H-NMR (400 MHz, CDCl$_3$) δ 1.21 (3H, d), 1.4-1.6 (4H, m), 2.6-3.0 (2H, brs), 3.67 (2H, m), 3.86 (1H, m).

Example 4

Production of (S)-1,4-pentanediol

Recombinant Escherichia coli HB101 (pNTRS) with an accession number of FERM BP-08545 was inoculated in 50 mL of 2×YT medium (tripeptone 1.6%, yeast extract 1.0%, NaCl 0.5%, zinc sulfate heptahydrate 50 mg, pH=7.0) that was sterilized in a 500-mL Sakaguchi flask, followed by shaking culture at 30° C. for 40 hours. Subsequently, 1,000 units of glucose dehydrogenase (manufactured by Amano Enzyme Inc.), an aqueous solution (64 g) containing 5.0 g of 5-hydroxy-2-pentanone produced in Example 2, 2.5 mg of NAD, 13.2 g of glucose were added to 50 mL of the resulting culture solution. The solution was stirred at 30° C. for 24 hours while the pH of the solution was adjusted to 6.5 by adding a 7.5 M aqueous solution of sodium hydroxide dropwise. After the reaction, 100 mL of ethyl acetate was added to the reaction solution to perform an extraction. The organic layer was distilled off under a reduced pressure, and the product was then purified by silica gel column chromatography. Thus, 5.0 g of oily (S)-1,4-pentanediol was obtained (yield: 100%). The optical purity of the product was measured by the same method as that in Example 1. The product had an optical purity of 99% ee or more.

Example 5

Production of (S)-1,4-bis(methanesulfonyloxy)pentane

A solution containing 2.5 g (24 mmol) of (S)-1,4-pentanediol produced in Example 3, 7.3 g (72 mmol) of triethylamine, and 30 mL of ethyl acetate was cooled to 5° C. Subsequently, 6.6 g (58 mmol) of methanesulfonyl chloride was added to the solution, and the solution was stirred for one hour. The solution was washed by adding 15 mL of a saturated aqueous solution of sodium hydrogencarbonate. The organic layer was further washed with 15 mL of water, and was dried over anhydrous magnesium sulfate. The solvent was then distilled off under a reduced pressure. Thus, (S)-1,4-bis(methanesulfonyloxy)pentane was obtained as a light yellow oily substance (6.1 g, yield; 98%).

$^1$H-NMR (400 MHz, CDCl$_3$) δ 1.45 (3H, d), 1.7-2.0 (4H, m), 3.03 (6H, s), 4.27 (2H, m), 4.86 (1H, m).

Example 6

Production of (R)-1-benzyl-2-methylpyrrolidine

First, 2.49 g (9.6 mmol) of (S)-1,4-bis(methanesulfonyloxy)pentane produced in Example 5 and 5.13 g (47.9 mmol) of benzylamine were stirred at 70° C. for three hours. Subsequently, 30 mL of ethyl acetate and 4.0 g of a 20 weight percent aqueous solution of sodium hydroxide were added to the mixture to perform an extraction. The organic layer was concentrated under a reduced pressure to obtain a yellow oily substance. This product was purified by silica gel column chromatography. Thus, (R)-1-benzyl-2-methylpyrrolidine was obtained as a light yellow oily substance (1.83 g, yield: 100%).

$^1$H-NMR (400 MHz, CDCl$_3$) δ 1.17 (3H, d), 1.45 (1H, m), 1.6-1.8 (2H, m), 1.93 (1H, m), 2.09 (1H, dd), 2.38 (1H, dq), 2.89 (1H, dd), 3.13 (1H, d), 4.02 (1H, d), 7.2-7.4 (5H, m).

The invention claimed is:

1. A process for producing an optically active 1,4-pentanediol represented by formula (2):

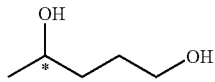
(2)

(wherein * represents an asymmetric carbon atom) comprising asymmetrically reducing 5-hydroxy-2-pentanone represented by formula (1):

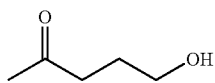
(1)

wherein said asymmetric reduction of 5-hydroxy-2-pentanone represented by formula (1) is catalyzed by an enzyme comprising the amino acid sequence of the reducing enzyme encoded by a vector selected from the group consisting of: pNTS1G of *Escherichia coli* HB101 (pNTS1G) (FERM BP-5835); pNTFPG of *Escherichia coli* HB101 (pNTFPG) (FERM BP-7117); pNTDRG1 of *Escherichia coli* HB101 (pNTDRG1) (FERM BP-08458); pNTRS of *Escherichia coli* HB101 (pNTRS) (FERM BP-08545); or pNTRGG1 of *Escherichia coli* HB101 (pNTRGG1) (FERM BP-7858).

2. The process according to claim 1, wherein the asymmetric reduction of 5-hydroxy-2-pentanone represented by formula (1) is catalyzed by an enzyme comprising the amino acid sequence of the reducing enzyme encoded by pNTRS of *Escherichia coli* HB101 (pNTRS) (FERM BP-08545), or pNTRGG1 of *Escherichia coli* HB101 (pNTRGG1) (FERM BP-7858).

3. The process according to claim 1, wherein 5-hydroxy-2-pentanone represented by said formula (1) produced by hydrolyzing 2-acetyl-γ-butyrolactone represented by formula (5):

(5)

in the presence of an acid is used as a starting material.

* * * * *